United States Patent [19]

Kelley et al.

[11] Patent Number: 4,849,181
[45] Date of Patent: * Jul. 18, 1989

[54] HEAT ACTIVATED DISPENSER FOR VAPORIZABLE MATERIALS

[75] Inventors: John Kelley, Phoenix; Timothy D. Kelley, Scottsdale, both of Ariz.

[73] Assignee: LAD Technology, Phoenix, Ariz.

[*] The portion of the term of this patent subsequent to Dec. 9, 20003, has been disclaimed.

[21] Appl. No.: 803,094

[22] Filed: Nov. 27, 1985

[51] Int. Cl.$^4$ .................. G05D 23/185; A61L 9/01
[52] U.S. Cl. .................................. 422/109; 422/124; 422/125; 422/126; 422/305; 219/274; 219/275; 239/54; 239/60
[58] Field of Search ................... 422/124–126, 422/305, 109; 239/54, 60; 219/271, 274, 275, 542; 126/427, 451

[56] References Cited

U.S. PATENT DOCUMENTS

| | | | |
|---|---|---|---|
| 2,468,164 | 4/1949 | Brewster | 422/305 |
| 2,539,696 | 1/1951 | Morrison | 422/305 |
| 2,942,090 | 6/1960 | Diehl | 422/125 |
| 3,248,530 | 4/1966 | Titmas | 422/125 |
| 3,895,928 | 7/1975 | Moran | 422/125 |
| 3,903,699 | 9/1975 | Davis | 219/378 |
| 3,948,445 | 4/1976 | Andeweg | 422/125 |
| 3,959,642 | 5/1976 | Turro | 422/125 |
| 4,346,059 | 8/1982 | Spector | 422/125 |
| 4,588,874 | 5/1986 | Napierski | 219/274 |
| 4,627,963 | 12/1986 | Olson | 422/125 |

FOREIGN PATENT DOCUMENTS 829494  6/1938  France .................. 422/305

OTHER PUBLICATIONS

Hackh's Chemical Dictionary, pp. 63 and 610, 1969.

Primary Examiner—Barry S. Richman
Assistant Examiner—Timothy M. McMahon
Attorney, Agent, or Firm—Harry M. Weiss

[57] ABSTRACT

According to the present invention there is provided an improved heat activated dispenser for releasing a vaporizable material into the ambient atmosphere. The inventive heat activated dispenser is made of a material which imparts excellent thermal insulating properties which control the rate of vaporization and provides a long useful life of the dispenser. Due to the novel use of absorbent compactable materials, such as synthetic silicates, the present invention utilizes no binders and substrates. Rather, the dispenser, according to the present invention, is an integral self-supporting structure. The nature of the absorbent compactable material used, makes the use of a novel method of manufacture especially advantageous. According to the novel method of manufacture, there is provided a compaction apparatus for compacting the absorbent compactable material, such as synthetic silicate, into the integral self-supporting structure of the heat activated dispenser. A volume of the absorbent compactable material is impregnated with the desired vaporizable material and added to the compaction apparatus, an additional volume of dry absorbent compactable material may be added. The absorbent compactable materials in the compaction apparatus are pre-formed, then compacted under a pressure sufficient to compact the materials into an integral self-supporting structure.

73 Claims, 3 Drawing Sheets

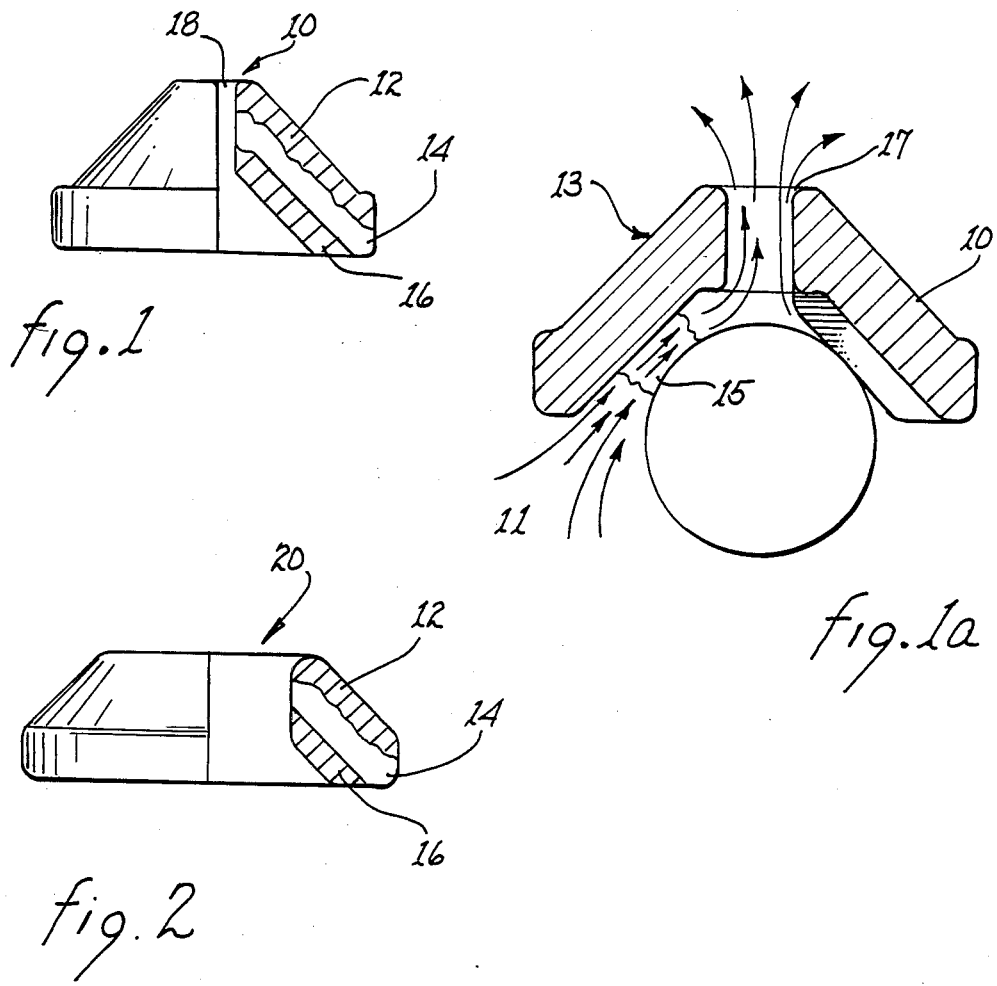
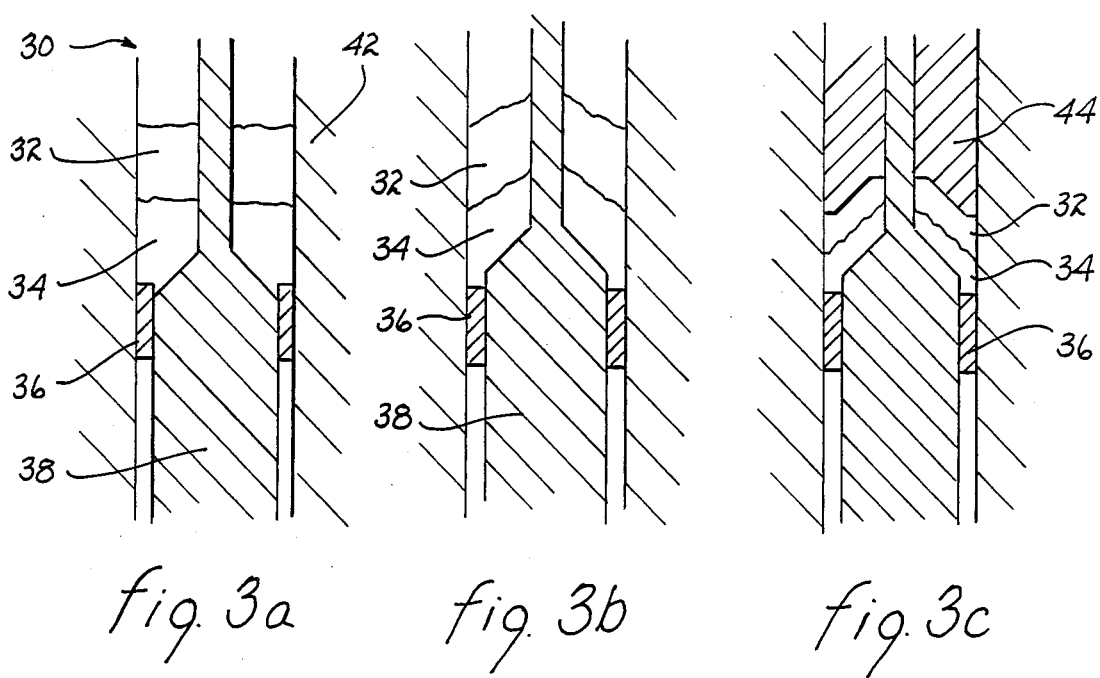

HEAT ACTIVATED DISPENSER FOR VAPORIZABLE MATERIALS

REFERENCE TO RELATED APPLICATIONS

This application relates to commonly assigned U.S. Pat. No. 4,627,963, Issued Dec. 9, 1986, Inventor: Donald M. Olson, entitled: Heat ActivatedDispenser and Method of Dispensing a Vapor Therefrom. The drawings and specification of that patent application are hereby specifically incorporated by reference.

BACKGROUND OF THE INVENTION

This invention relates generally to dispensers for releasing vaporizable materials into the ambient atmosphere. More particularly, the present invention relates to improvements in heat activated dispensers for releasing vaporizable materials such as fragrances, medications, insecticides or any other desired vaporizable material into the ambient. The present invention also relates generally to a method of manufacture of the inventive heat activated dispenser which provides a dispenser consisting of a unitary self-supporting structure thereby alleviating the necessity of utilizing a substrate, binder or other foreign support structures.

It has been found desirable to provide a dispenser for vaporizable materials which has an extensive useful life while being capable of providing a sustained long-term release of the desired vaporizable material in to the ambient. Additionally, a desirable dispenser should be capable of being utilized with a wide range of vaporizable materials having a broad range of uses. The inventive dispenser should, ideally, be capable of holding a relatively large volume or weight of vaporizable material such as vaporizable liquids having a wide range of viscosities or vaporizable powders, be capable of operating with high temperatures, be thermally insulating for safe handling and controlling the rate of vaporization and be biodegradeable. Further, the inventive dispenser should be capable of receiving heat from an a heat source and be of a configuration adapted to fit over, around or in between, such that it accepts heat from the suitable heat source, such as an ordinary household lightbulb while fitting within the inner configuration of a majority of lamp fixtures commonly found within a home. Finally, the inventive dispenser should be capable of resting on or around the suitable heat source and have a configuration suitable for channeling the generated heat across the inner surface area of the dispenser and into the ambient.

In order to achieve the aforementioned desired properties, it is preferable to utilize a synthetic silicate such as that currently marketed by the Manville Corporation under the trade mark "MICRO-CEL". The useful synthetic silicates are, by nature, very fluffy. This property makes them a very difficult material to handle and prepare. Typically, conventional devices utilize some type of substrate or binder to hold or contain a powdery or fibrous absorbent non-formable material. Conventional absorbant devices and absorbent materials are inadequate because they do not hold sufficient volumes or weights of the vaporizable material, they are non-formable and, therefore, need binders or substrates, or if they are capable of being molded, these devices do not hold sufficient quantities of vaporizable material. The inventive method of manufacturing the inventive dispenser solves the problem of having to use a substrate or binder to support a powdery or fibrous absorbent material. It has been found that the synthetic silicates are capable of being compacted into certain shapes and will become a self-supporting structure when so compacted. Therefore, the method of manufacture of the inventive dispenser is designed to account for the chemical and physical properties of the useful synthetic silicates.

SUMMARY OF THE INVENTION

Accordingly, it is an object of the present invention to provide a heat activated dispenser for releasing vaporizable materials into the ambient atmosphere.

It is another object of the present invention to provide a heat activated dispenser which is capable of holding a vaporizable material, gradually releasing quantities of the vaporizable material and having a long useful life.

It is a further object of the present invention to provide a heat activated dispenser which is fabricated of a material which is highly absorbent and will absorb a wide range of vaporizable materials having a wide range of viscosities and has controllable porosity.

It is a still further object of the present invention to provide a heat activated dispenser which will operate at high temperatures and is thermally insulating for safe handling and controlling the rate of vaporization.

It is yet a further object of the present invention to provide a heat activated dispenser which is immediately biodegraded.

It is still another object of the present invention to provide a material for use in making the heat activated dispenser which is highly absorbent, thermally insulating, immediately biodegraded and capable of being compacted into a self-supporting structure.

It is yet another object of the present invention to provide a method of manufacturing the inventive heat activated dispenser which entails the controlled compaction of the material for use in making the heat activated dispenser as a self-supporting structure.

It is yet another object of the present invention to provide a method of manufacturing the inventive heat activated dispenser which provides for a substantially uniform density of the material used in making the heat activated dispenser The foregoing and other objects, features and advantages of the present invention will be apparent from the following, more particular description of the preferred embodiments of the invention as illustrated in the accompanying drawings.

BRIEF DESCRIPTION OF THE DRAWINGS

FIG. 1 is a partial cross-section side elevational view of a heat activated dispenser according to the present invention. Additionally FIG. 1 of U.S. patent application Ser. No. 584,826 is hereby specifically incorporated by reference.

FIG. 1a is a partial cross-sectional side elevational view of a heat activated dispenser adapted to fit over a lightbulb, and the path of air from intake to exhaust.

FIG. 2 is a partial cross-sectional side elevational view of a heat activated dispenser according to the present invention.

FIGS. 3a, 3b and 3c are cross-sectional sequential side elevational views of a press and die illustrating the method of making a heat activated dispenser according to the present invention.

DESCRIPTION OF THE PREFERRED EMBODIMENTS

Figure 4:
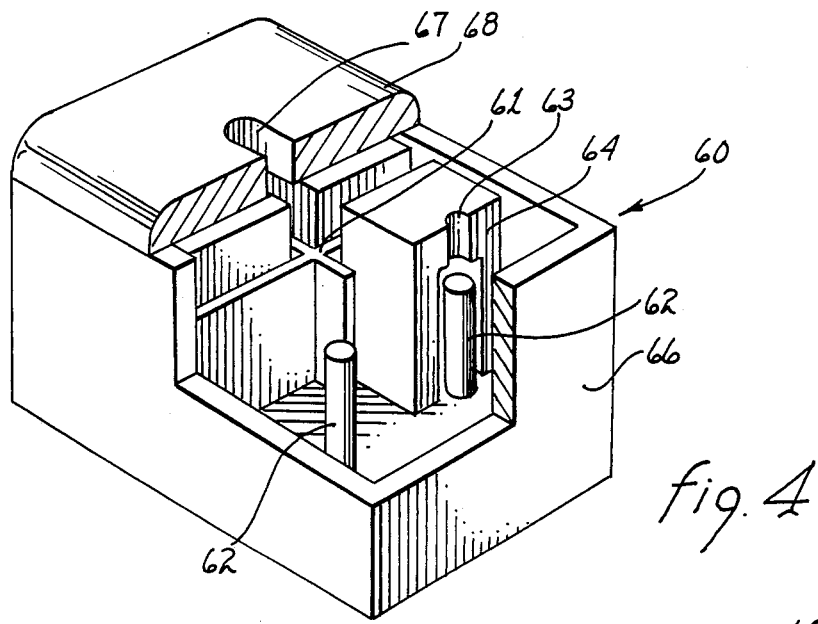
FIG. 4 is a partially cut-away, partial cross-sectional perspective view of an alternate embodiment of the present invention showing an environmental dispenser having a plurality of heating elements, a plurality of heat activated dispensers according to the present invention and a vented container provided therewith.

FIG. 1 illustrates a heat activated dispenser 10 according to the present invention. The general structure and configuration of heat activated dispenser 10 is disclosed with reference to FIGS. 1 and 2, and the accompanying specification, of U.S. Pat. No. 4,627,963 which is incorporated by reference. Heat activated dispenser 10 is made of any material which will suitably absorb or adsorb a wide range of vaporizable materials, which is thermally insulating and which is capable of being compacted into a self-supporting structure of uniform density. In the preferred embodiment, dispenser 10 is made of synthetic silicates, preferably one of the hydrous calcium silicates marketed by the Manville Corporation under the trademark "MICRO-CEL". MICRO-CEL is marketed in a variety of different grades each grade having different chemical and physical properties. It has been found that all grades of MICRO-CEL are suitable for use in the present invention, however, Grade E exhibits superior characteristics when used in the present invention.

Dispenser 10 is made in such a manner as to consist of, essentially, a two layer integral structure. Outer layer 12 is the silicate layer which is impregnated with the vaporizable material which is to be released into the ambient. Inner layer 14 is a layer of dry non-impregnated silicate. The configuration of dispenser 10 is may be adapted to fit upon the spherical part of an ordinary lightbulb. Support rib 16 serves to support the dispenser 10 upon a heat source, such as a lightbulb. Venturi channels, not shown, are disposed between support ribs 16 and form an air inlet near the base of dispenser 10. These venturi channels serve to pump out fragrance and accelerate the heated air past the lightbulb which acts to maintain a cooler operating temperature of the lightbulb and provides for a longer lightbulb operating life. Exhaust vent 18 allows heated air to escape through the exhaust vent 18 and into the ambient atmosphere.

Referring to FIG. 1a, which shows the path of the intake air 11, the accelerated air 15 and the exhaust air 17. This air flow creates a pressure differential between the ambient and the air flow. This pressure differential causes the heated vaporizable material 13 to be drawn through the dry inner silicate layer 14 into the air flow and causes the air flow to become mixed with the vaporizable material released into the ambient atmosphere.

FIG. 2 is an alternate embodiment of the present invention showing a heat activated dispenser 20 having two compacted layers. Outer layer 12 is a silicate layer impregnated with the desired vaporizable material. Inner layer 14 is a dry silicate layer which thermally insulates the impregnated outer layer 12 from the heat of the heat source. The configuration of dispenser 20 is adapted to fit upon the spherical part of an ordinary lightbulb and accept heat therefrom. Support ribs 16 support dispenser 20 upon the lightbulb. The air flow described above in reference to FIG. 1a is also present with dispenser 20.

FIGS. 3a, 3b and 3c illustrate the inventive method of manufacturing dispensers 10 and 20. The manufacturing apparatus 30 for making the dispensers consists, generally, of a press and die. Press and die apparatus 30 is configured to produce any desired shape for the dispenser unit. The method of manufacturing the inventive dispensers is sequentially illustrated by FIGS. 3a–c. A dry silicate layer 34 may be added initially into the apparatus 30, this layer conforms to the general shape of the die 38 and the outer wall 42 of apparatus 30. The ejector ring 36 is in an elevated position.

Where the heat activated dispenser is to be used with a high temperature heat source, two layers of silicate are used, first the dry silicate layer 34 will be added, followed by the layer of silicate impregnated with the vaporizable material 34. However, where the heat activated dispenser is to be used with a lower temperature heat source, it is sufficient to use one layer consisting entirely of silicate which is impregnated with the vaporizable material 34.

The blending of the liquid vaporizable material with the synthetic silicate is especially critical. Ideally, any mixture of vaporizable material and silicate may be used so long as the vaporizable material is absorbed or adsorbed into the silicate. However, in practice, it has been found that the ratios of blends in the range of about 1:1 to 4:1 are provide the best results, preferably the ratio of vaporizable material to synthetic silicate is about 4:1. Uniform blending is crucial to the present invention because a liquid vaporizable material is not freely permeable among the cell walls of the synthetic silicates. Therefore, the vaporizable material must be blended with the synthetic silicate to insure that each cell of synthetic silicate is exposed to the vaporizable material.

FIG. 3b illustrates the pre-forming step to shape the single or double layer of synthetic silicate. For purposes of illustration only, reference is made to the method of manufacture utilizing the double layer of synthetic silicate. It should be noted, however, that the method is equally applicable regardless of whether the single or double layer method is actually used. The pre-forming occurs when ejector ring 36 is lowered to its resting position. Lower layer of dry silicate material 34 is lowered into a generally conical shape which conforms to the configuration of the die 38. The upper surface of dry layer 34 becomes slightly sloped. Impregnated layer 32 is also lowered into a generally conical shape having sloped upper and lower areas. It is important to create this pre-shaped sloped arrangement of the non-compacted layers. The fluffy nature of the silicates makes it very difficult to compact without losing material through pressure relief upon compaction. Therefore, the lowering of the ejector ring causes air to be relieved from the material thereby minimizing the compaction of any air remaining in the silicate material. Moreover, this pre-forming facilitates the compaction of the synthetic silicate without causing undue external or internal stress on any one part of the dispenser. By relieving external and internal stresses otherwise present in the compaction process, the pre-forming step facilitates achieving a uniform density throughout the compacted dispenser unit.

Uniform density is achieved through providing a uniform compaction ratio in the press and die apparatus. Additionally, the substantially symmetrical configuration of the dispenser, and of the material within the press and die apparatus, lends itself to providing the necessary uniform density throughout the dispenser. It is critical that a uniform density is achieved. It has been found that in the absence of a substantially uniform density, the resulting dispenser unit is highly prone to fracturing.

FIG. 3c illustrates the compaction process. Press 44 having the configuration of top surface of the desired dispenser is lowered at a proper pressure and compacts the impregnated layer 32 and the dry layer 34 into a unitary structure. The compaction is carried out at any pressure such that the integrity of the material used to make the dispenser is not destroyed. The self-supporting unitary structure of the heat activated dispenser is facilitated by compacting the synthetic silicate material to a uniform density under a uniform compaction ratio.

The preferable synthetic silicate material, MICRO-CEL, is used because it is capable of being compacted into a solid self-supporting structure. The use of the synthetic silicates permits the elimination of substrates and binders which are conventional in the art. Further, the use of synthetic silicates, in particular MICRO-CEL, greatly facilitates the maintenance of uniformity between the impregnated outer layer 32 and the inner dry layer 34. It has been found that other materials tend to fracture at the junction of the impregnated outer layer 32 and the inner dry layer 34. This fracturing is not found when the synthetic silicates are employed.

In a preferred embodiment of the present invention there is provided a heat activated dispenser which has a configuration adapted to accept heat from a lightbulb, as is illustrated by FIGS. 1 and 2. Ideally, the inventive dispenser depicted in FIGS. 1 and 2 will be capable of being used with a wide variety of light fixtures. Therefore, it has been found necessary to configure the dispenser so that it will fit within the majority of lamp harps of conventional light fixtures. Accordingly, the height and diameter of the inventive dispensers 10 and 20 of FIGS. 1 and 2 must meet with certain height and diameter restrictions corresponding to the majority of the lamp harps. The inventive dispenser configured to accept heat from a lightbulb should have a radius no greater than 3.5 inches, and a height no greater than 2.34 inches measured from the center point of the spherical portion of the lightbulb.

An alternate embodiment of the present invention for releasing a relatively greater volume of vaporized material is illustrated in FIG. 4. FIG. 4 shows a container 66 divided into multiple chambers by insulating dividing wall 61. Each chamber has within it a heating element 62 for heating a heat activated dispenser 64 which is situated within the chamber. Heating element 62 may be any suitable heating element, but preferably is a resistive heating element which may be automatically or manually regulated by, forexample, a rheostat or thermostat. Each heat activated dispenser has an exhaust aperture 63 from which the vaporized material impregnated into the dispenser is released. Vent aperture 67 in container top 68 exhausts the cumulative vaporized material released form each of the plurality of heat activated dispensers 64. The alternate embodiment illustrated in FIG. 4 may be capable of operating from either an alternating or direct current electrical source.

Figure 5:
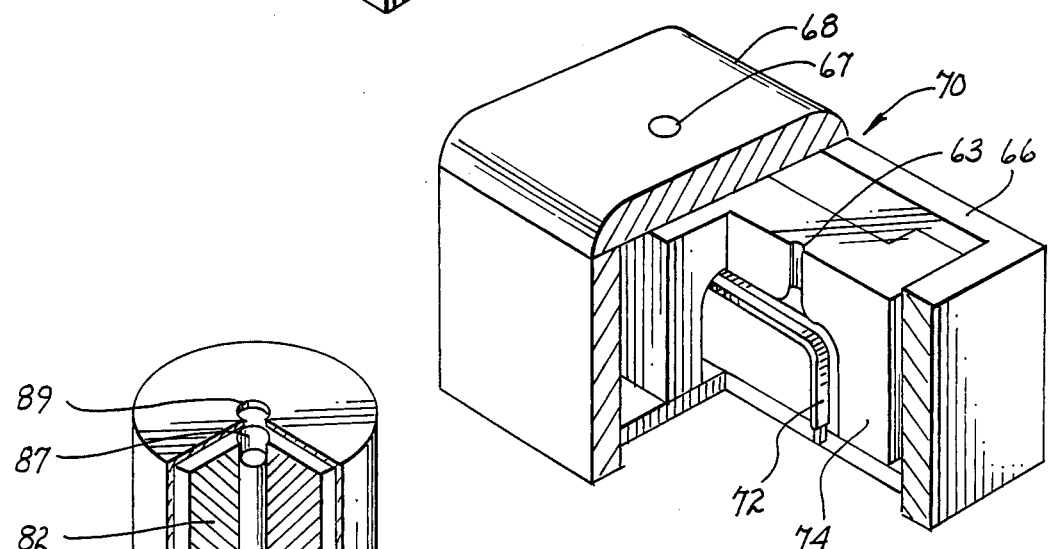
FIG. 5 is a partially cut-away, partial cross-sectional perspective view of an alternate embodiment of the heat activated dispenser showing a heating element, a heat activated dispenser according to the present invention and a vented container provided therewith.

Another preferred embodiment of the present invention is illustrated by FIG. 5. According to this preferred embodiment, there is provided a heat activated dispenser 70 which consists of an outer container 66 having a container top 68. Container top 68 has a vent aperture 67 for releasing the vaporized material impregnated into heat activated dispenser 74. Heat activated dispenser 74 is situated within container 66 and is configured to accept heat from heating element 72. Heating element 72 may be any suitable heating element, but preferably is a resistive heating element which may be automatically or manually regulated by, for example, a rheostat or thermostat, and be capable of accepting electricity from an alternating or direct current electrical source. Heat activated dispenser 74 has an exhaust aperture 63 for venting the vaporized material impregnated into the synthetic silicate material of the dispenser 74.

Figure 6:
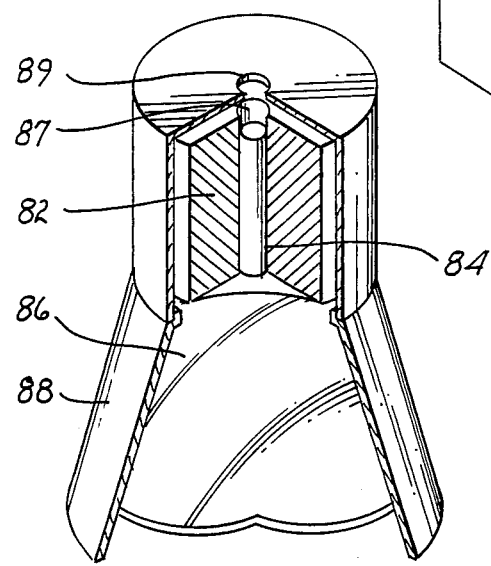
FIG. 6 is a partially cut-away, partial cross-sectional perspective view of an alternate embodiment of the heat activated dispenser showing a solar powered dispenser having a concave mirror lens, a clear lens for admitting light, a heating element, a heat activated dispenser according to the present invention and a vented container provided therewith.

In another alternate preferred embodiment of the present invention, illustrated by FIG. 6, there is provided a solar powered heat activated dispenser 80. The solar powered heat activated dispenser 80 consists of a heat activated dispenser unit 82 made of synthetic silicates according to the inventive method of manufacture noted above. Dispenser unit 82 is situated within an upper chamber of the solar powered dispenser 80. Mirror lens 86 gathers ambient light which enters through clear lens 88. The mirror lens 86 is configured such that its focal point focuses solar light on heat base and rod 84 which conducts heat and transmits the heat into exhaust aperture 87. The vaporizable material impregnated into the heat activated dispenser 82 is vaporized by the transmitted heat and released through vent opening 89 into the ambient.

Figure 7:
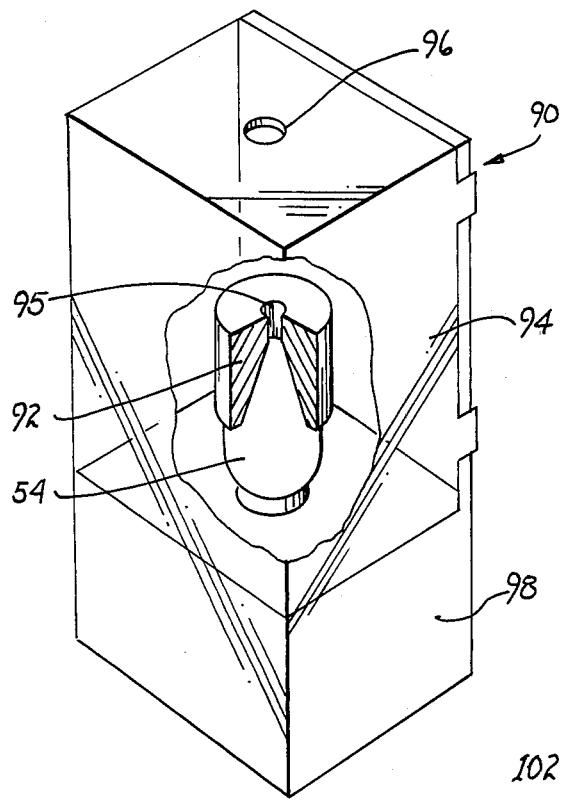
FIG. 7 is a partially cut-away, partial cross-sectional perspective view of an alternate embodiment of the present invention showing a night light dispenser having a lightbulb, a heat activated dispenser according to the present invention and a vented nightlight container provided therewith.

FIG. 7 illustrates another preferred embodiment consisting of a night-light heat activated dispenser for releasing a vaporizable material into the ambient. According to this embodiment of the invention there is provided a night-light heat activated dispenser 90 consisting of an outer container 94 having a base 98 capable of accepting an electric current from any alternating or direct current electrical source. Outer container 94 has a vent opening 96 which releases the volatilized material from the container and into the ambient. The night-light light bulb 54 is the heat source for heating the heat activated dispenser 92 which rests upon the night-light light bulb 54. Heat from the night-light light bulb 54 sets up an air flow which operates substantially similarly to the air flow described with reference to FIG. 1a. This air flow causes the vaporized material to be exhausted through exhaust opening 95 and then through vent opening 96 in outer container 94.

Figure 8:
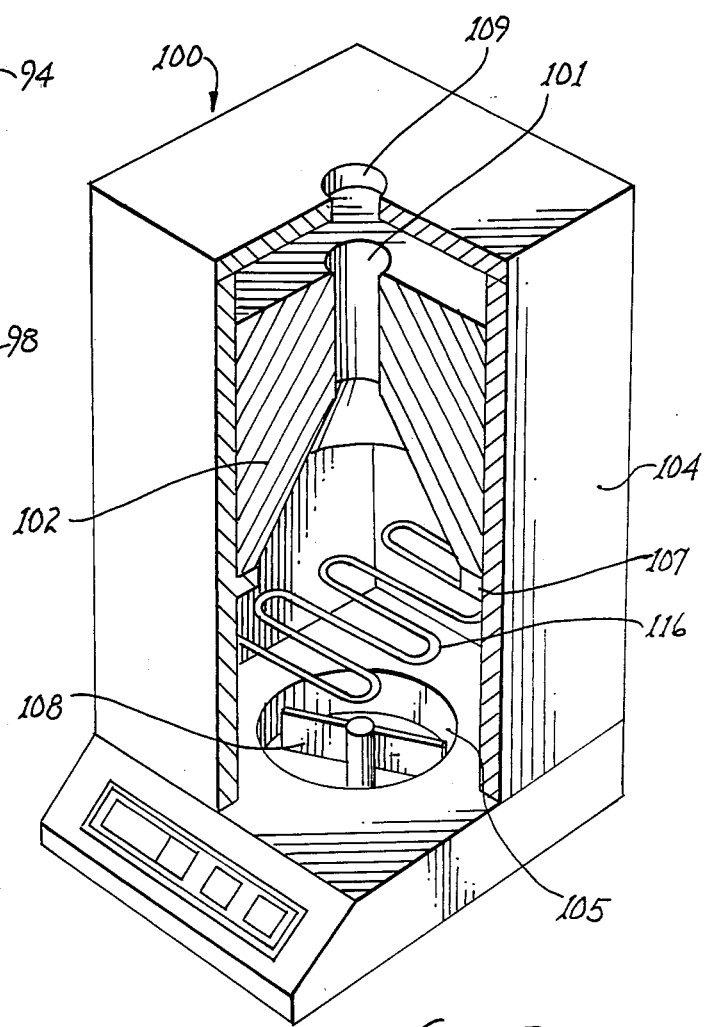
FIG. 8 is a partially cut-away, partial cross-sectional perspective view of an alternate embodiment of the present invention showing a forced air unit having a heating element, an air inlet, a fan for drawing in air and forcing it by the heating element, a heat activated dispenser according to the present invention and a vented container provided therewith.

A forced air heat activated dispenser according to the present invention is depicted in FIG. 8. The forced air heat activated dispenser 100 according to the present invention consists of an outer container 104 having an interior support flange 107 or other suitable means for supporting the heat activated dispenser unti 102 within the container. A fan 108 situated in an aperture 105 of container 104 draws ambient air into dispenser 100. Heating element 106, which may be any suitable heating element, preferably a resistive heating element capable of being automatically or manually regulated by, for example, a rheostat of thermostat, capable of accepting electricity from an alternating or direct current electrical source. Heating element 106 heats the air drawn into container 104 by fan 108. This heated air passes through an aperture 101 of heat activated dispenser unit 102 and sets up the air flow described with reference to FIG. 1a, which causes the vaporizable material to be vaporized and released into the ambient through vent opening 109.

Figure 9:
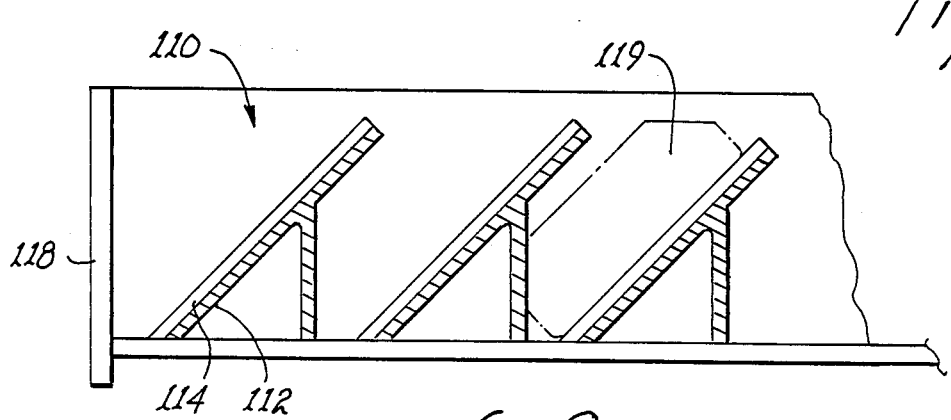
FIG. 9 is a cross-sectional side-elevational view of an alternate embodiment of the present invention showing a heating register capable of accepting a plurality of heat activated dispensers according to the present invention and having a plurality of resistive heating elements and corresponding stands contained within a vented container.

Finally, in another preferred embodiment of the present invention, shown in FIG. 9, there is provided a heat activated dispenser array apparatus 110 capable of accepting a plurality of heat activated dispenser units 119, shown in phantom. Support members 112 provide support for the heat activated dispenser units 119 as well as heating elements 114. Heating elements 114 may consist of any suitable heating elements, but preferably resistive heating elements are employed which are capable of accepting electricity from an alternating or direct current electrical source and which are manually or automatically regulated by, for example, a rheostat or thermostat. An outer container 118 provides an outer enclosure for the plurality of support members 112, heating elements 114 and dispenser units 119. The heat generated by heating element 114 sets up an air flow similar to that described with reference to FIG. 1a above. This air flow causes the release of the vaporizable material from the dispenser unit 116 into the ambient atmosphere.

In each of the preferred embodiments having an outer container it is desirable to situate the heat activated dispenser within the outer container in such a manner as to have the top surface of the dispenser immediately adjacent to the top inner surface of the container. It has been found that condensation will form if there is an air space between the top surface of the dispenser and the top inner surface of the container. This condensation may impede the operation of the heat activated dispenser apparatus. To further facilitate the elimination of condensation within the apparatus, it has been found desirable to have the vent aperture of the outer container be slightly larger in diameter than the exhaust vent aperture (illustrated as 18 in FIG. 1, 17 in FIG. 1a, 20 in FIG. 2, 63 in FIGS. 4 and 5, 87 in FIG. 6, 95 in FIG. 7, or 101 in FIG. 8) of the heat activated dispenser.

While the invention has been particularly shown and described in reference to the preferred embodiments thereof, it will be understood by those skilled in the art that changes in form and details may be made therein without departing from the spirit and scope of the invention.

What is claimed is:

1. An improved heat activated dispenser apparatus for releasing a material into the ambient, comprising: a volume of a dry synthetic silicate and a volume of synthetic silicate impregnated with a vaporizable material to be released into the ambient; said dry volume and said impregnated volume further being compacted into a solid generally frustro-conical shape having an upper opening and a lower opening thereof, adapted to accept heat from a heat source.

2. The improved heat activated dispenser according to claim 1 wherein said synthetic silicate further comprises hydrous calcium silicate.

3. The improved heat activated dispenser according to claim 1 wherein said dry volume and said impregnated volume are compacted
   in a press and die apparatus configured to any shape suitable for said heat activated dispenser
   and are compacted at a pressure suitable to retain the integrity of the compacted synthetic silicate material, to form said heat activated dispenser.

4. A heat dispenser apparatus according to claim 3 wherein said heat activated dispenser is compacted by pre-forming said layers of synthetic silicate by lowering a inner retaining ring prior to compacting said layers in said press and die apparatus.

5. A heat activated dispenser apparatus according to claim 1, wherein said apparatus is configured to accept heat from a lightbulb.

6. A heat activated dispenser apparatus according to claim 5, wherein said apparatus is configured to fit within a lamp harp of a light fixture.

7. A heat activated dispenser apparatus according to claim 1, wherein said dispenser apparatus further comprises:
   an outer container having at least one vent aperture passing therethrough;
   at least one compacted shape of said synthetic silicates disposed within said container; and
   at least one heating element disposed in such a manner as to transfer heat to each of said compacted shapes.

8. The heat activated dispenser apparatus according to claim 7, wherein said outer container further comprises a plurality of inner chambers disposed therein and a top member having a vent aperture passing therethrough; at least one of said heating elements being disposed in each of said plurality of inner chambers; and each of said compacted shapes of synthetic silicates disposed in each of said plurality of inner chambers and configured to accept said at least one heating element.

9. The heat activated dispenser apparatus according to claim 7, wherein said at least one heating element further comprise resistive heating elements.

10. The heat activated dispenser apparatus according to claim 7, wherein said outer container further comprises an upper and a lower chamber; said lower chamber further comprising light transmitting means for allowing light to enter said chamber and lens means for fucusing said light; said upper chamber further comprising heat generating means integral with a heating element for receiving said focused light from said lens means, generating heat therefrom and transmitting heat from said heat generating means into said upper chamber, said compacted shape of said synthetic silicate being disposed in close proximity to and immediately superior to said heating element, and a vent aperture in said upper chamber.

11. The heat activated dispenser apparatus according to claim 7, wherein said outer container further comprises an electrical means for operably engaging an ordinary household electrical outlet, and a vent aperture passing therethrough; said heating element further comprises a low wattage lightbulb; and said compacted shape of said synthetic silicate is shaped to accept heat from said low wattage lightbulb.

12. The heat activated dispenser apparatus according to claim 7, wherein said outer container further comprises an air inlet aperture having fan means disposed therein for drawing ambient air into said outer container and forcing the ambient air across said heating element thereby heating the air.

13. The heat activated dispenser apparatus according to claim 7, wherein said apparatus further comprises a plurality of heating elements, a plurality of support member means for supporting said plurality of heating elements, thereon, said plurality of heating elements being disposed adjacent to said support member means, and a plurality of said compacted shapes of said synthetic silicates each of said plurality of compacted shapes of synthetic silicate blend disposed in close proximity and immediately superior to each of said plurality of heating elements.

14. An improved heat activated dispenser apparatus, comprising:
    an outer container;
    a top operably coupled to said outer container and having a vent aperture passing therethrough;
    a plurality of inner chambers disposed within said outer container;
    a plurality of heating elements, each of which is disposed in each of said plurality of inner chambers;
    control means for regulating the temperature of said plurality of heating elements; and
    a plurality of heat activated dispensers comprising an integral self-supporting structure made of a compactable absorbent material having a vaporizable material impregnated therein for releasing said vaporizable material into the ambient, each of said plurality of heat activated dispensers being disposed in close proximity to each of said plurality of heating elements and adapted to accept heat from said one of a plurality of heating elements.

15. The improved heat activated dispenser apparatus according to claim 14, wherein each of said plurality of heat activated dispensers further comprises: a volume of dry absorbent compactable material and a volume of absorbent compactable material impregnated with a vaporizable material to be released into the ambient; said dry material and said impregnated material further being compacted into an integral self-supporting structure.

16. The improved heat activated dispenser apparatus according to claim 14, wherein each of said plurality of heat activated dispensers further comprises: a volume of absorbent compactable material impregnated with a vaporizable material to be released into the ambient; said impregnated material further being compacted into an integral self-supporting structure.

17. The improved heat activated dispenser apparatus according to claim 14, wherein said plurality of heating elements comprise resistive heating elements adapted to accept an electrical current from an alternating or direct current electrical source and said control means further comprises an automatic temperature regulator.

18. The improved heat activated dispenser apparatus according to claim 14, wherein said dry absorbent compactable material further comprises synthetic silicates.

19. An improved heat activated dispenser apparatus, comprising:
    a container having an upper and a lower chamber;
    light transmitting means for allowing light to enter said lower chamber of said container;
    lens means disposed in said lower chamber of said container for focusing the light;
    heat generating means, interdisposed between said upper chamber and said lower chamber of said container, for receiving said focused light and generating heat therefrom;
    a heating element thermally coupled to said heat generating means and disposed within said upper chamber of said container for generating heat therefrom and transmitting heat from said heat generating means into said upper chamber of said container;
    a heat activated dispenser comprising an integral self-supporting structure made of a compactable absorbent material having a vaporizable material impregnated therein for releasing said vaporizable material into the ambient configured to accept heat from said heating element disposed within said upper chamber of said container; and
    a vent aperture in said container.

20. The improved heat activated dispenser apparatus according to claim 19, wherein said heat activated dispenser further comprises: a volume of dry absorbent compactable material and a volume of absorbent compactable material impregnated with a vaporizable material to be released into the ambient; said dry material and said impregnated material further being compacted into an integral self-supporting structure.

21. The improved heat activated dispenser apparatus according to claim 19, wherein said heating elements comprise resistive heating elements capable of accepting an electrical current from an alternating or direct current electrical source.

22. The improved heat activated dispenser apparatus according to claim 19, wherein said dry absorbent compactable material further comprises synthetic silicates.

23. An improved heat activated dispenser apparatus, comprising:
    an outer container having electrical means for operably accepting an electrical current from an alternating or direct current electrical source, a vent aperture passing therethrough;
    a heating source electrically coupled to said electrical means; and
    a heat activated dispenser comprising an integral self-supporting structure made of a compactable absorbent material having a vaporizable material impregnated therein for releasing said vaporizable material into the ambient, shaped to accept heat from said heat source and disposed in close proximity and immediately superior to said heat source.

24. The heat activated dispenser apparatus according to claim 23, wherein said heating source further comprises a low-wattage lightbulb.

25. The improved heat activated dispenser apparatus according to claim 23, wherein each of said plurality of heat activated dispensers further comprises: a volume of absorbent compactable material impregnated with a vaporizable material to be released into the ambient;

said impregnated material further being compacted into an integral self-supporting structure.

26. The heat activated dispenser apparatus according to claim 23, wherein said dry absorbent compactable material further comprises synthetic silicate.

27. An improved heat activated dispenser apparatus, comprising:
a container;
an air inlet aperture in said container and passing therethrough;
fan means disposed within said air inlet aperture for drawing ambient air into said container and increasing the velocity thereof through said container;
a heating element disposed within said container for heating said air drawn by said fan means into said container;
control means for regulating the temperature of said heating element; and
a heat activated dispenser comprising an integral self-supporting structure made of a compactable absorbent material having a vaporizable material impregnated therein for releasing a vaporizable material into the ambient shaped to accept and channel said heated air into the ambient, said heat activated dispenser being disposed above and in close proximity to said heating element.

28. The heat activated dispenser apparatus according to claim 27, wherein said heating element further comprises a resistive heating element capable of accepting an electrical current from an alternating or direct current electrical source and said control means further comprises an automatic temperature regulator.

29. The heat activated dispenser apparatus according to claim 27, wherein said absorbent compactable material further comprises synthetic silicate.

30. An improved heat activated dispenser apparatus, comprising:
a plurality of support members;
a plurality of heating elements each of which is supported by each of said plurality of support members;
control means for regulating said plurality of heating elements; and
a plurality of heat activated dispensers comprising an integral self-supporting structure made of a compactable absorbent material having a vaporizable material impregnated therein each of which is disposed in close proximity to each of said plurality of heating elements.

31. The heat activated dispenser apparatus according to claim 30, wherein said plurality of heating elements further comprises a plurality of resistive heating elements capable of accepting an electrical current from an alternating or direct current electrical source and said control means further comprises an automatic temperature regulator.

32. The heat activated dispenser apparatus according to claim 30, wherein each of said plurality of heat activated dispensers further comprises: a volume of dry absorbent compactable material and a volume of absorbent compactable material impregnated with a vaporizable material to be released into the ambient; said dry material and said impregnated material further being compacted into an integral self-supporting structure.

33. The improved heat activated dispenser apparatus according to claim 30, wherein each of said plurality of heat acivated dispensers further comprises: a volume of absorbent compactable material impregnated with a vaporizable material to be released into the ambient; said impregnated material further being compacted into an integral self-supporting structure.

34. The heat activated dispenser apparatus according to claim 30, wherein said absorbent compactable material further comprises synthetic silicate.

35. An improved heat activated dispenser apparatus for releasing a material into the ambient, comprising: a volume of synthetic silicate impregnated with a vaporizable material to be released into the ambient; said impregnated volume further being compacted into a solid generally frustroconical shape having an upper opening and a lower opening thereof, adapted to accept heat from a heat source.

36. The improved heat activated dispenser according to claim 35, wherein said synthetic silicate further comprises synthetic hydrous calcium silicate.

37. The improved heat activated dispenser according to claim 35, wherein said impregnated volume are compacted in a press and die apparatus configured to any shape suitable for said heat activated dispenser
and are compacted at a pressure suitable to retain the integrity of the compacted synthetic silicate material.

38. The heat activated dispenser apparatus according to claim 37, wherein said heat activated dispenser is compacted by performing said layers of absorbent material by lowering a retaining ring prior to compacting said absorbent material.

39. A heat activated dispenser apparatus according to claim 35, wherein said apparatus is configured to accept heat from a lightbulb.

40. A heat activated dispenser apparatus according to claim 39 wherein said apparatus is configured to fit within a lamp harp of a light fixture.

41. A heat activated dispenser apparatus according to claim 35, wherein said dispenser apparatus further comprises:
an outer container having at least one vent aperture passing therethrough;
at least one compacted shape of said synthetic silicates disposed within said container; and
at least one heating element disposed in such a manner as to transfer heat to each of said compacted shapes.

42. The heat activated dispenser apparatus according to claim 41, wherein said outer container further comprises a plurality of inner chambers disposed therein and a top member having a vent aperture passing therethrough; each of said heating elements being disposed in each of said plurality of inner chambers; and each of said compacted shapes of synthetic silicates disposed in each of said plurality of inner chambers and configured to accept heat at least one of said heating elements.

43. The heat activated dispenser apparatus according to claim 41, wherein said heating elements further comprise resistive heating elements capable of accepting an electrical current from an alternating or direct current electrical source.

44. The heat activated dispenser apparatus according to claim 41, wherein said outer container further comprises an upper and a lower chamber; said lower chamber further comprising light transmitting means for allowing light to enter said chamber and lens means for focusing said light; said upper chamber further comprising heat generating means integral with a heating element for receiving said focused light from said lens means, generating heat therefrom and transmitting heat from said heat generating means into said upper chamber, said compacted shape of said synthetic silicate being disposed in in close proximity with and disposed immediately superior to said heating element, and a vent aperture in said upper chamber.

45. The heat activated dispenser apparatus according to claim 41, wherein said outer container further comprises an electrical means for electrically coupling to an electrical source and a vent aperture passing therethrough; said heating element further comprises a low wattage lightbulb; and said compacted shape of said synthetic silicate is shaped to accept heat from said low wattage lightbulb.

46. The heat activated dispenser apparatus according to claim 41, wherein said outer container further comprises an air inlet aperture having fan means disposed therein for drawing ambient air into said outer container and forcing the ambient air across said heating element thereby heating the air.

47. The heat activated dispenser apparatus according to claim 41, wherein said apparatus further comprises a plurality of support member means for supporting a plurality of said heating elements thereon, said plurality of heating elements being disposed adjacent to said support member means, and a plurality of said compacted shapes of said synthetic silicates each of said plurality of compacted shapes of synthetic silicate blend disposed in in close proximity with and immediately superior to each of said heating elements.

48. An improved heat activated dispenser apparatus, comprising:
an outer container having a vent aperture passing therethrough;
a heating element disposed within said outer container;
a heat activated dispenser comprising an integral self-supporting structure made of a compactable absorbent material having a vaporizable material impregnated therein, adapted to accept heat from said heating element and release said vaporizable material into the ambient, said heat activated dispenser further being disposed within said outer container in such a manner as to have an upper surface of said heat activated dispenser situated immediately adjacent to an upper surface of said outer container having said vent aperture passing therethrough.

49. The improved heat activated dispenser apparatus for releasing a material into the ambient according to claim 48 wherein said heat activated dispenser further comprises: a volume of a dry synthetic silicate and a volume of synthetic silicate impregnated with a vaporizable material to be released into the ambient; said dry volume and said impregnated volume further being compacted into a shape suitably configured to accept heat from any suitable heat source.

50. The improved heat activated dispenser according to claim 48 wherein said synthetic silicate further comprises hydrous calcium silicate.

51. The improved heat activated dispenser according to claim 48 wherein said dry volume and said impregnated volume are compacted
in a press and die apparatus configured to any shape suitable for said heat activated dispenser
and are compacted at a pressure suitable to retain the integrity of the compacted synthetic silicate material.

52. A heat activated dispenser apparatus according to claim 48, wherein said dispenser apparatus further comprises:
at least one compacted shape of said synthetic silicates disposed within said container; and
at least one heating element disposed in such a manner as to transfer heat to each of said compacted shapes.

53. The heat activated dispenser apparatus according to claim 48, wherein said outer container further comprises a plurality of inner chambers disposed therein and a top member having a vent aperture passing therethrough; each of said heating elements being disposed in each of said plurality of inner chambers; and each of said compacted shapes of synthetic silicates disposed in each of said plurality of inner chambers and configured to accept heat at least one of said heating elements.

54. The heat activated dispenser apparatus according to claim 48, wherein said heating elements further comprise resistive heating elements.

55. The heat activated dispenser apparatus according to claim 48, wherein said outer container further comprises an upper and a lower chamber; said lower chamber further comprising light transmitting means for allowing light to enter said chamber and lens means for focusing said light; said upper chamber further comprising heat generating means integral with a heating element for receiving said focused light, generating heat therefrom and transmitting heat from said heat generating means into said upper chamber, said compacted shape of said synthetic silicate being disposed in close proximity with and immediately superior to said heating element, and a vent aperture in said upper chamber.

56. The heat activated dispenser apparatus according to claim 48, wherein said outer container further comprises an electrical means for operably engaging an ordinary household electrical outlet, and a vent aperture passing therethrough; said heating element further comprises a low wattage lightbulb; and said compacted shape of said synthetic silicate is shaped to accept heat from said low wattage lightbulb.

57. The heat activated dispenser apparatus according to claim 48, wherein said outer container further comprises an air inlet aperture having fan means disposed therein for drawing ambient air into said outer container and forcing said ambient air across said heating element thereby heating said air.

58. A heat activated dispenser apparatus according to claim 48 wherein the heat source is a lightbulb.

59. A heat activated dispenser apparatus according to claim 58, wherein said apparatus is configured to accept heat from a lightbulb.

60. A heat activated dispenser apparatus according to claim 58, wherein said apparatus is configured to fit within a lamp harp.

61. The improved heat activated dispenser apparatus for releasing a material into the ambient according to claim 48, wherein said heat activated dispenser further comprises: a volume of synthetic silicate impregnated with a vaporizable material to be released into the ambient; impregnated volume further being compacted into a shape suitably configured to accept heat from a suitable heat source.

62. The improved heat activated dispenser according to claim 61, wherein said synthetic silicate further comprises hydrous calcium silicate.

63. A heat activated dispenser according to claim 61 wherein said heat activated dispenser is compacted by preforming said layers of synthetic silicate by lowering a retaining ring prior to compacting said layers.

64. A heat activated dispenser apparatus according to claim 61, wherein said dispenser apparatus further comprises:
- at least one compacted shape of said synthetic silicates disposed within said container; and
- at least one heating element disposed in such a manner as to transfer heat to each of said compacted shapes.

65. The heat activated dispenser apparatus according to claim 61, wherein said outer container further comprises a plurality of inner chambers disposed therein and a top member having a vent aperture passing therethrough; each of said heating elements being disposed in each of said plurality of inner chambers; and each of said compacted shapes of synthetic silicates disposed in each of said plurality of inner chambers and configured to accept heat at least one of said heating elements.

66. The heat activated dispenser apparatus according to claim 61, wherein said heating elements further comprise resistive heating elements capable of accepting an electrical current from an alternating or direct current electrical source.

67. The heat activated dispenser apparatus according to claim 61, wherein said outer container further comprises an upper and a lower chamber; said lower chamber further comprising light transmitting means for allowing light to enter said chamber and lens means for focusing said light; said upper chamber further comprising heat generating means integral with a heating element for receiving said focused light, generating heat therefrom and transmitting heat from said heat generating means into said upper chamber, said compacted shape of said synthetic silicate being disposed in close proximity with and immediately superior to said heating element, and a vent aperture in said upper chamber.

68. The heat activated dispenser apparatus according to claim 61, wherein said outer container further comprises an electrical means for electrically coupling to an electrical source and a vent aperture passing therethrough; said heating element further comprises a low wattage lightbulb; and said compacted shape of said synthetic silicate is shaped to accept heat from said low wattage lightbulb.

69. The heat activated dispenser apparatus according to claim 61, wherein said outer container further comprises an air inlet aperture having fan means disposed therein for drawing ambient air into said outer container and forcing said ambient air across said heating element thereby heating said air.

70. The improved heat activated dispenser according to claim 61, wherein said impregnated volumes are compacted
- in a press and die apparatus configured to any shape suitable for said heat activated dispenser
- and are compacted at any pressure suitable to retain the integrity of the compacted synthetic silicate material.

71. A heat activated dispenser apparatus according to claim 70, wherein the heat source is a lightbulb.

72. A heat activated dispenser apparatus according to claim 71, wherein said apparatus is configured to accept heat from a lightbulb.

73. A heat activated dispenser apparatus according to claim 71, wherein said apparatus is configured to fit within a lamp harp of a light fixture.

* * * * *